United States Patent [19]

Blumenfeld et al.

[11] Patent Number: 5,115,580

[45] Date of Patent: May 26, 1992

[54] METHOD AND APPARATUS FOR DRYING HAND COVERINGS

[76] Inventors: Charles M. Blumenfeld, 4700 Parkridge Rd., Sacramento, Calif. 95822; Barbara M. Koell, 2116 Kinsington St., West Sacramento, Calif. 95691

[21] Appl. No.: 714,911

[22] Filed: Jun. 13, 1991

[51] Int. Cl.$^5$ ............................................. F26B 25/00
[52] U.S. Cl. .......................................... 34/104; 34/106
[58] Field of Search ................... 34/103, 104, 239, 21, 34/106; 223/78, 79, 80, 52

[56] References Cited

U.S. PATENT DOCUMENTS

| | | | |
|---|---|---|---|
| 276,768 | 5/1883 | Calderwood | 223/79 |
| 754,539 | 3/1904 | Burr | 34/103 |
| 1,338,031 | 4/1920 | Messinger | 34/103 |
| 1,450,033 | 3/1923 | Gowan | 34/104 |
| 1,475,193 | 11/1923 | Meegan . | |
| 2,076,735 | 4/1937 | Leindorf | 34/26 |
| 2,340,206 | 1/1944 | Richards | 34/104 |
| 2,565,455 | 8/1951 | Miller | 34/104 |
| 2,614,337 | 10/1952 | Darbo | 34/104 |
| 3,166,439 | 1/1965 | Dennhofer | 34/104 |
| 3,645,009 | 2/1972 | Ketchum | 34/104 |
| 4,085,519 | 4/1978 | Masika | 34/104 |
| 4,265,030 | 5/1981 | Smallegan | 34/104 |
| 4,464,796 | 8/1984 | Heissenberger et al. | 223/78 |
| 4,596,078 | 6/1986 | McCartney | 34/104 |
| 4,967,060 | 10/1990 | Lomeli | 392/384 |
| 5,003,707 | 4/1991 | Chu | 34/104 |

*Primary Examiner*—Henry A. Bennet
*Assistant Examiner*—Denise L. F. Gromada
*Attorney, Agent, or Firm*—Christie, Parker & Hale

[57] ABSTRACT

Apparatus for drying a hand covering with a wrist portion includes a closure which makes a snug fit within the wrist portion. An inlet aperture is connected to a source of drying gas, which inflates the hand covering. One or more outlet ports through the closure permits vapor-laden gas to leave the interior of the hand covering. Restrictive means limit the flow of gas from the hand covering to ensure full inflation. In terms of method, a wet hand covering, which includes a finger section and an elastomeric wrist portion, is dried by inserting a closure in the wrist portion. A drying gas is injected through an inlet aperture in the closure and into the hand covering at a sufficient rate and temperature to inflate the finger section and vaporize liquid. Vapor-laden gas is removed from the hand covering through an outlet aperture in the closure.

13 Claims, 3 Drawing Sheets

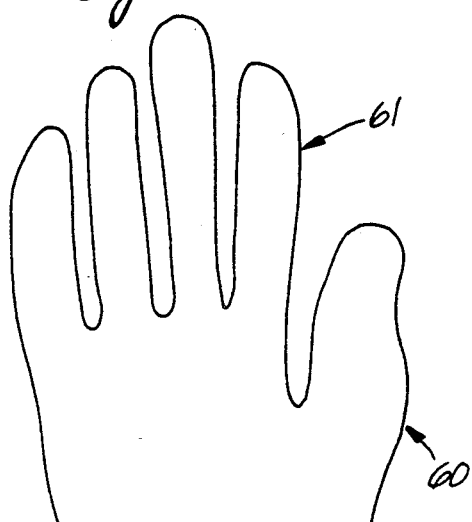
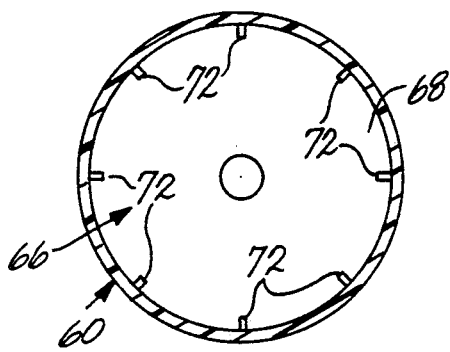
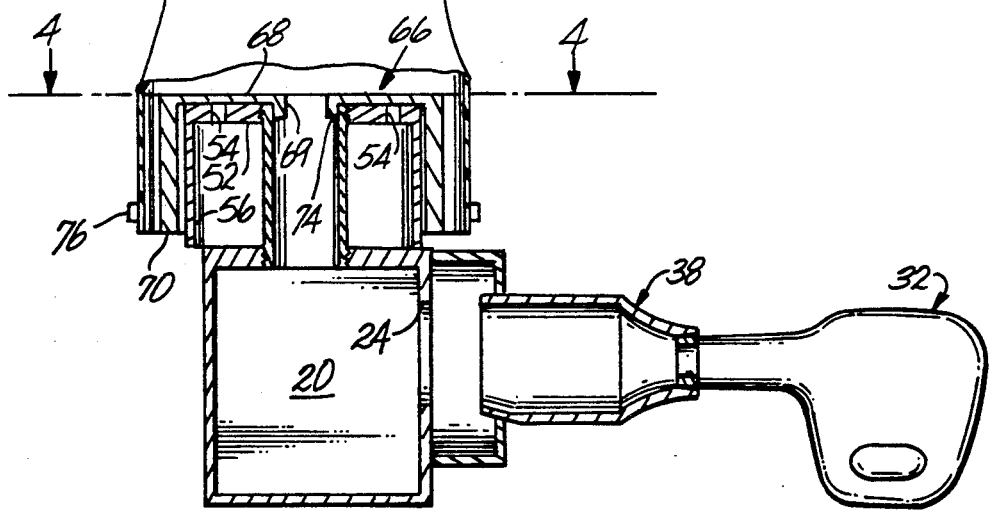

METHOD AND APPARATUS FOR DRYING HAND COVERINGS

BACKGROUND OF THE INVENTION

This invention provides apparatus and methods for drying hand coverings, such as gloves and mittens.

The invention is well-suited for drying all types of hand coverings, especially flexible elastomeric gloves such as surgical gloves and gloves used by beauty parlor operators. Some surgical gloves are relatively expensive, but have been routinely discarded because there has not been any economical way to wash and dry them. Gloves used by beauty parlor operators are not particularly expensive and, therefore, have been routinely discarded after a single use. Such practice is not only an economic waste, but adds to disposal problems.

This invention provides inexpensive, versatile apparatus for drying hand coverings of various types and sizes so that virtually all hand coverings which have been previously discarded after a single use may now be washed and economically dried for repeated reuse.

SUMMARY OF THE INVENTION

In terms of apparatus for drying a flexible, elastomeric hand covering with a wrist portion, the invention includes a closure adapted to make a snug fit within the wrist portion of the hand covering. The closure includes an inlet aperture adapted to be connected to a source of drying gas under pressure. One or more outlet apertures through the closure permits gas to flow from the interior of the hand covering.

Preferably, the total effective cross sectional area of the inlet aperture is at least equal to, or greater than, the total effective cross sectional area of the outlet aperture so that it is relatively easy to introduce the drying gas at a rate which causes the hand covering to assume a substantially fully-inflated position, thereby accelerating the drying of the hand covering. The snug fit made by the wrist portion around the closure prevents the incoming heated gas from blowing the hand covering off the closure. If needed, the wrist portion of the hand covering can be clamped to the closure by a rubber band, or the like.

In a preferred form of the invention, the closure is annular, and the inlet aperture is located in a central portion of the closure. A plurality of outlet ports extend through the closure around the inlet aperture and are spaced at equal intervals to provide an annular exit path for vapor-laden drying gas from the hand cover fitted over the closure. In one form, the closure includes an annular skirt with means for blocking a major portion of the cross sectional area of the skirt against flow of gas from the volume enclosed between the skirt and the closure. For drying a number of hand coverings simultaneously, the invention preferably includes a plurality of closures, each with a separate respective inlet connected to the source of drying gas. Conveniently, the closures are mounted on a chamber with an opening adapted to be connected to the discharge of a conventional electrically-heated air blower. If needed, a blower adapter provides for connecting the chamber inlet to blower nozzles of different sizes. A closure adapter is also provided to fit around the closure to accommodate hand coverings with wrist portions of various sizes.

In terms of method for drying a flexible hand covering which includes a finger section and an elastomeric wrist portion, the invention includes securing the wrist portion to make a snug fit around a closure. A drying gas is injected through an inlet aperture in the closure and into the hand covering at a sufficient rate to inflate the finger section. Vapor-laden gas is removed from the hand covering through at least one outlet aperture in the closure to cause the hand covering to dry. Preferably, the drying gas is injected into a central part of the wrist portion of the hand covering and is removed by annular flow in an area surrounding the inlet aperture.

DESCRIPTION OF THE DRAWINGS

FIG. 3 is a view similar to FIG. 2, but includes an adapter around the closure for handling larger-sized hand coverings;

FIG. 4 is a view taken on line 4—4 of FIG. 3; and

DETAILED DESCRIPTION

Figure 1:
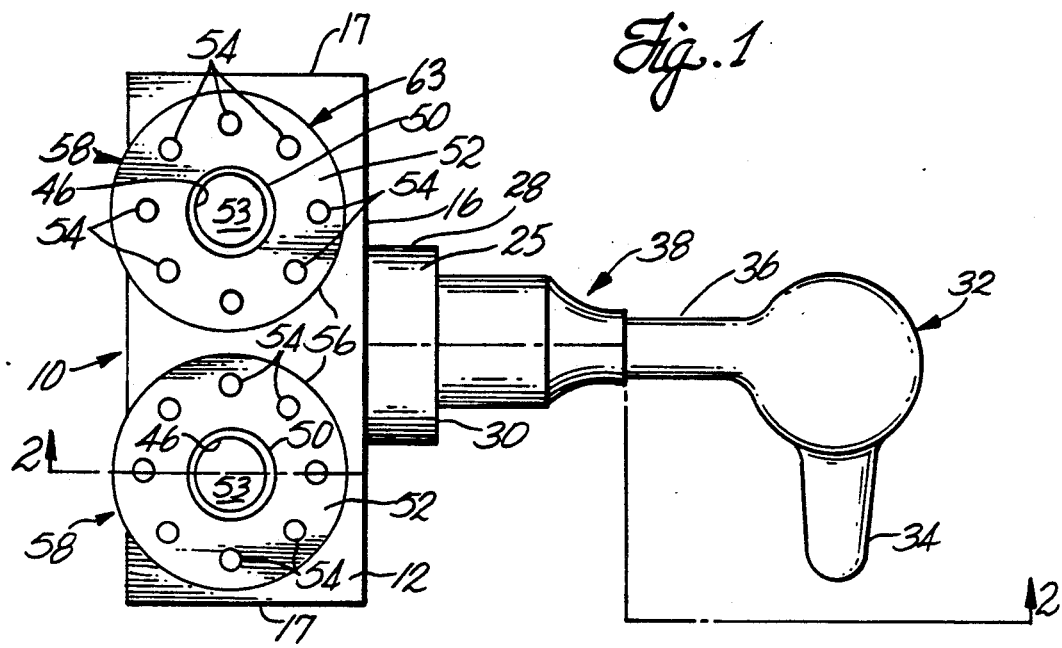
FIG. 1 is a plan view of a presently preferred embodiment of the invention without a hand covering in place for drying.
Figure 2:
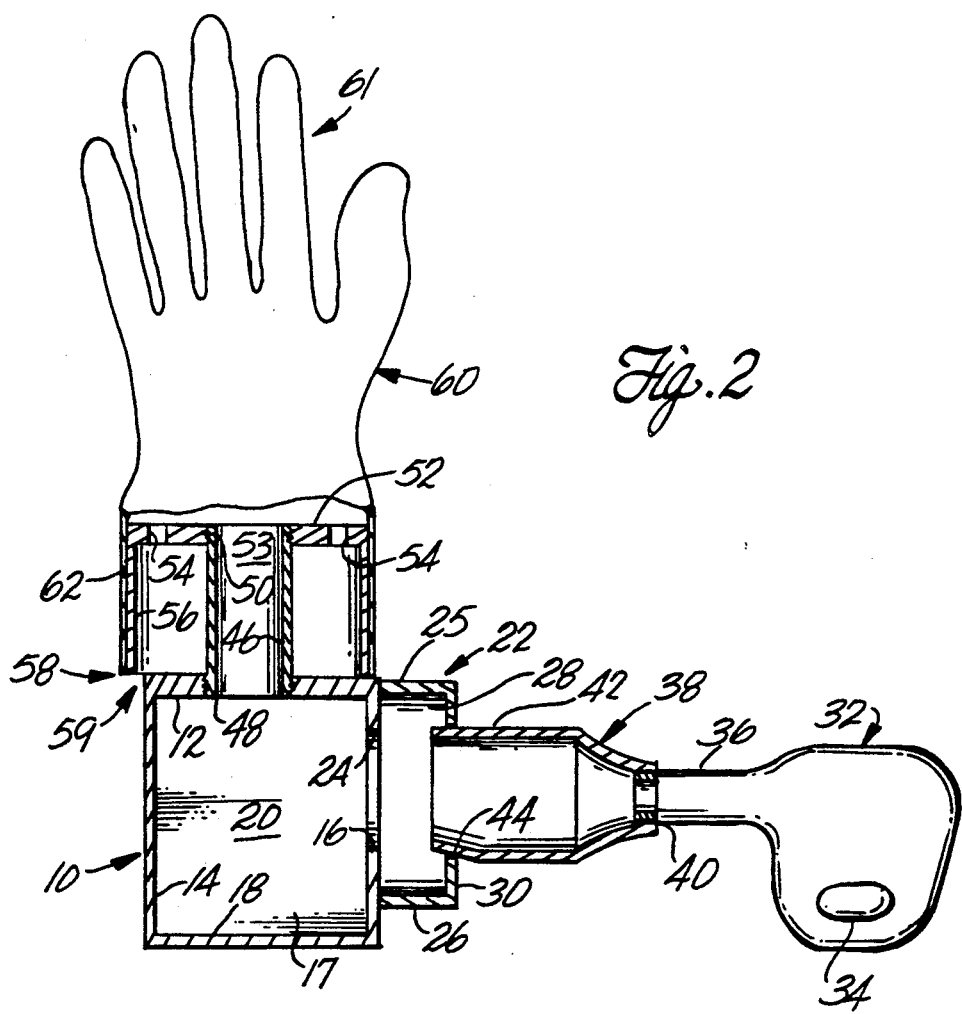
FIG. 2 is a view taken on staggered line 2—2 of FIG. 1 with a hand covering in place for drying.

Referring to FIGS. 1 and 2, a rectangular box 10 includes a flat top 12, a first sidewall 14, a second sidewall 16, end walls 17, and a flat bottom 18 to form an enclosed chamber 20.

A square-shaped compartment 22 is secured to the exterior of sidewall 16 over a circular inlet port 24 in the sidewall. The compartment includes a top wall 25, a bottom wall 26, end walls 28, and an outside wall 30.

A conventional electrically heated to air blower 32 includes a handle 34 and a discharge nozzle 36 disposed in a blower adapter 38 having a circular and inwardly tapering inlet port 40 which makes a snug friction fit around the discharge nozzle 36. The adapter tapers outwardly away from the blower and terminates in a straight cylindrical section 42, which makes a snug fit in a circular and inwardly tapering port 44 in the outer wall 30 of the compartment so that warm dry air can be forced from the blower into the chamber 20 through inlet port 24. The blower adapter is not used with a blower (not shown) which has a larger diameter discharge nozzle of such size as to make a snug fit in port 40.

The lower end of a vertical pipe 46 is threaded into an opening 48 extending through the top wall of the chamber. The upper end of the vertical pipe 46 is threaded into a central opening 50 extending through the center of a horizontal, disk-shaped closure 52. The pipe and central opening 50 in the closure 52 provide an inlet aperture 53.

Eight ports 54 extend through the periphery of the closure and are spaced at 45° intervals. An annular skirt 56, formed integrally with the periphery of the disk, extends downwardly so that the lower edge of the skirt rests on the top surface of the top wall 12 of the box, except for a small arcuate section 58 of the skirt which overhangs sidewall 14 of the box, leaving a relatively small outlet aperture 59 (FIG. 2) through which gas can flow to the atmosphere by leaving the space enclosed by the closure, skirt 56, and top wall of the box (see FIG. 2). The area of the outlet aperture 59 is substantially less than the cross sectional area of the inlet aperture 53 formed by the central opening 50 in the closure.

As shown in FIG. 2, a flexible elastomeric hand covering 60, say, a surgical glove, includes a finger section 61 and a wrist portion 62, which is stretched to make a snug, sealing fit around the periphery of the closure 52 and the exterior surface of the skirt 56.

As shown in FIG. 1, a second closure 63 is mounted on the top wall of the box adjacent the first closure. The second closure and supporting structure is identical with the first and, therefore, is not described in detail for the sake of brevity. The box can be made as large as desired to accommodate as many closures as may be required to dry hand coverings simultaneously.

In using the apparatus shown in FIGS. 1 and 2, used gloves are cleaned, usually by washing in a suitable detergent, and then rinsed, say, in water. Each wet glove is stretched in its wrist portion to make a snug friction fit over a respective closure (as shown in FIG. 2). Thereafter, the blower nozzle is inserted, as shown in FIGS. 1 and 2, and the blower turned on to force warm or hot air into the chamber 20, and through the closure inlet aperture 53 at a rate which causes the glove mounted around the closure to assume a substantially fully-inflated position, as shown in FIG. 2. This is made possible by the snug friction fit of the wrist portion of the glove on the closure, and by the outlet aperture 59 imposing a sufficient back pressure on the gas flowing through it. The dry gas (usually air) jets upwardly into the inside of the finger portion 61 of the glove, and then flows outwardly and downwardly to leave through an annular flow area established by the outlet ports 58, which open into a flow channel formed by the annular interior of the skirt 56 surrounding the pipe 46, as shown in FIG. 2. The temperature of the drying gas is sufficient to volatilize the liquid (usually water) which wets the glove, and yet is not so hot as to damage the glove. Most gloves wet with water can be rapidly dried using warm air at a temperature between about 90° F and about 175° F.

The warm and moisture-laden gas leaves the interior of the skirt through the relatively small outlet aperture 59 under the skirt at the left (as viewed in FIG. 2) side of the box. The cross sectional area of the outlet aperture 59 is equal to or less than that of the inlet aperture 53 to ensure adequate inflation of the glove for efficient drying.

Thus, the glove is fully inflated so that drying gas circulates rapidly and freely throughout the entire interior portion of the hand covering. In addition, the drying gas heats the hand covering so that the exterior of the hand covering also dries rapidly. Since the glove is fully inflated, the finger section is held so that it also dries rapidly inside and out.

After the drying operation is completed, the air blower is turned off, the gloves removed for reuse. If required, the gloves can be sterilized by conventional procedures.

The apparatus shown in FIGS. 3 and 4 is substantially identical with that shown in FIGS. 1 and 2. FIG. 3 is substantially identical to FIG. 2, and the same reference numerals are used in FIG. 3 to identify elements corresponding to those shown in FIG. 2.

The apparatus of FIGS. 3 and 4 includes a cylindrical adapter 66, which has a circular, disk-shaped annular top wall 68 and a downwardly (as viewed in FIG. 3) extending annular skirt 70. The top wall 68 of the adapter rests on the upper surface of the disk-shaped closure 52 and blocks ports 54 extending through that closure. An inlet aperture 69 through top wall 68 is collinear with inlet aperture 53 of closure 52.

As can be seen best in FIG. 3, the external diameter of the adapter is greater than that of the skirt 56 attached to closure 52 so that the external surface of the skirt 70 makes a snug fit inside the wrist portion 62 of a glove of a larger size which would not make a snug fit around the exterior surface of skirt 56.

Four vertical (as viewed in FIG. 3) grooves 72 in the exterior surface of the adapter skirt 70 provide outlet apertures for warm gas to leave in a generally annular zone from the interior of the glove. The combined cross sectional area of grooves is equal to or less than that of either of the inlet apertures 53 or 69 to ensure full inflation of the glove.

The advantage of the apparatus shown in FIGS. 3 and 4 is not only that the adapter accommodates a glove with a larger wrist size than that possible for the apparatus of FIGS. 1 and 2, but the adapter shown in FIGS. 3 and 4 permits the wrist portion of the glove to be warmed and dried by hot air flowing through grooves 72, thus accelerating the drying of the wrist portion. The weight of the adapter can be sufficient to hold the inflated glove down in a position shown in FIG. 3. Alternatively, the central portion of the adapter top wall 68 includes a downwardly extending and externally threaded annular boss 74, which threads down into the upper end of threaded bore 50 in the closure 52.

Thus, with the adapter of the apparatus shown in FIGS. 3 and 4, the apparatus of FIGS. 1 and 2 can easily be modified to accommodate gloves with wrist portions of different sizes. If necessary, an adjustable clamp or rubber band 76 (FIG. 3) can be secured around the exterior of the wrist portion of the glove to anchor the glove in place while inflated with warm air.

Figure 5:
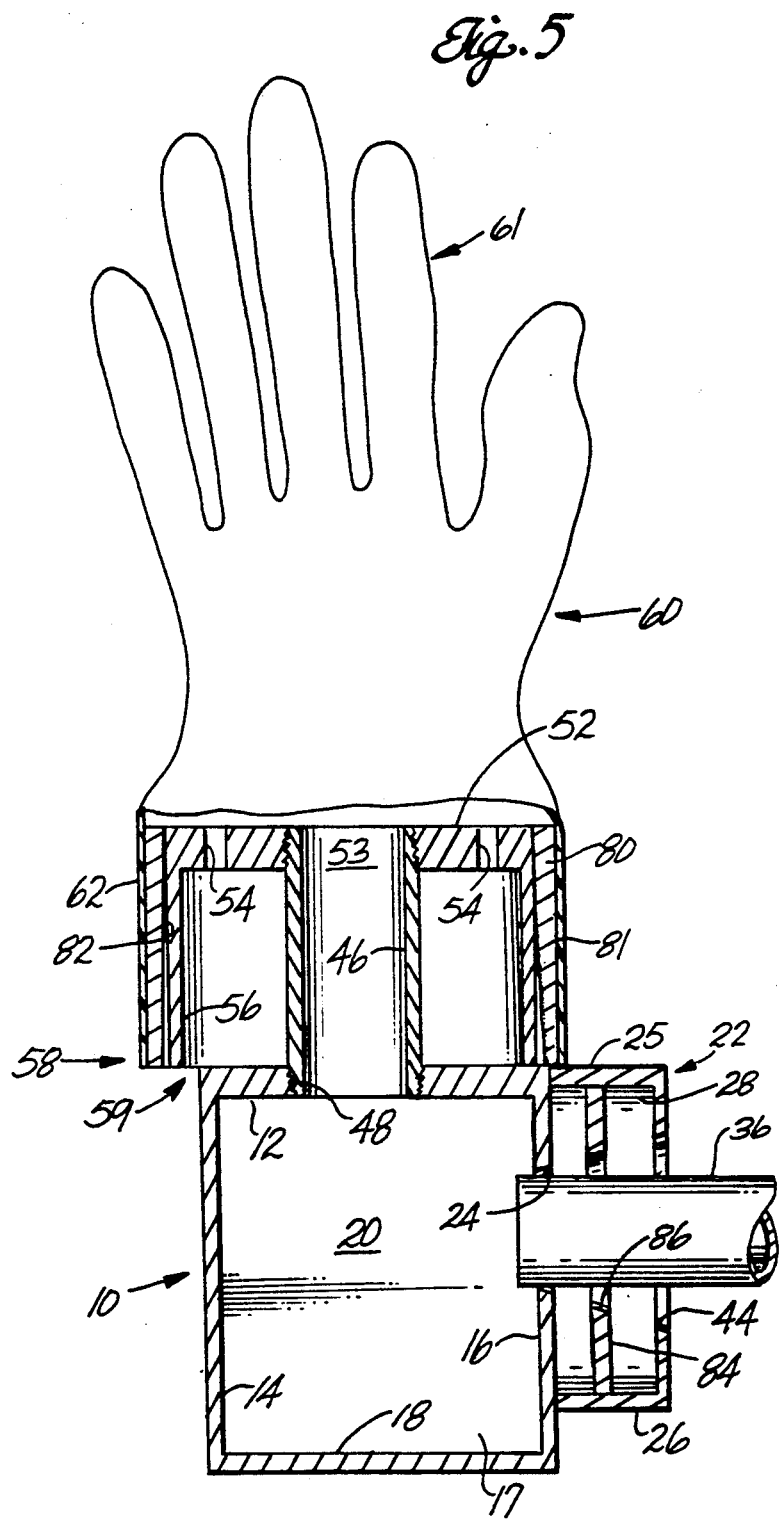
FIG. 5 is a view similar to FIG. 2, but showing an alternate form of adapters for accommodating hand coverings and blower nozzles of different sizes.

The apparatus of FIG. 5 is similar to that shown in FIGS. 1 and 2, and the same reference numerals are used in FIG. 5 to identify elements corresponding to those shown in FIGS. 1 and 2.

Referring to FIG. 5, a cylindrical closure adapter 80 in the form of an elongated collar open at each end includes a cylindrical outer surface 81 and a downwardly and outwardly tapering inner surface 82, which makes a snug slip fit around the exterior of the upper end of the closure 52. The external diameter of the closure adapter 80 is greater than that of the skirt 56, and therefore the external surface 81 of the closure adapter makes a snug fit inside the wrist portion 62 of a glove 60 of a larger size which would not make a snug fit around the exterior surface of skirt 56. Thus, the apparatus of FIG. 5 can easily be modified by the closure adapter 80 to accommodate hand coverings with wrist portions of different sizes. The square-shaped compartment 22 secured to the exterior of sidewall 16 includes a square-shaped internal partition 84, which is bonded around its edges to the internal surfaces of top, bottom, and sidewalls 25, 26, and 28 of compartment 22. The internal partition 84 is parallel to sidewall 30 of compartment 22 and sidewall 16 of box 10. The interior partition 84 includes a circular and inwardly tapering port 86 of a smaller diameter than port 44 in outside wall 30 of compartment 22. Circular inlet port 24 in sidewall 16 of the box is of a smaller diameter than port 86 of partition 84. Ports 24, 44, and 86 are dimensioned to make snug respective fits around blower nozzles of different sizes. As shown in FIG. 5, a blower nozzle 36 is of a size which passes through inlet ports 44 and 86, but makes a snug fit against the interior of tapered inlet port 24 in sidewall 16 of box 10.

The advantage of the embodiment shown in FIG. 5 is that no separate blower adapter is required for blower nozzles of different sizes. Instead, the ports 24, 44, and 86 are of dimensions which readily accommodate blower nozzles of the most common sizes.

Another advantage of the present invention is its modular construction, i.e., the sidewalls 14 and 16 can be omitted from a plurality of boxes, which can be bonded together to provide as many as closures as may be desired for drying a number of hand coverings simultaneously. The only requirement is that the outermost two boxes of the assembly be provided with the equivalent of sidewalls 14 and 16, constructed as shown in FIGS. 1, 2, 3, or 5. For large arrays of many boxes assembled as just described, appropriate sidewalls and compartments, such as sidewall 16 and compartment 22 shown in FIG. 5, can be provided to receive as many blowers as may be required to dry numerous hand coverings simultaneously.

The apparatus of this invention can be made of any suitable material. However, I have found that conventional sheets of acrylic butadiene styrene (ABS) and polyvinyl chloride (PV) pipe and fittings are well suited because they are easy to work, and can easily be bonded together by ethylene dichloride.

We claim:

1. Apparatus for drying a hand covering with a wrist portion, the apparatus comprising:
    a closure adapted to make a snug fit within the wrist portion of the hand covering;
    an inlet aperture through the closure and opening into the interior of the hand covering;
    an inlet conduit connected to the inlet aperture and adapted to be connected to a source of gas under pressure and thus permit gas to flow into the interior of the hand covering;
    an outlet port spaced from the inlet aperture and extending through the closure, the outlet port being connected to the atmosphere through a flow channel so the port and channel form an outlet flow path to the atmosphere to permit gas to flow from the interior of the hand covering; and
    means in the outlet flow path making the effective cross sectional area of the outlet flow path for gas flow less than that of the inlet aperture so the hand covering can be inflated by the discharge of gas from a conventional electrically heated blower.

2. Apparatus according to claim 1 in which the closure is substantially circular in cross section.

3. Apparatus according to claim 1 or 2 in which the inlet aperture is located in a central portion of the closure.

4. Apparatus according to claim 3 which includes a plurality of outlet ports around the periphery of the closure.

5. Apparatus according to claim 1 or 2 which includes a skirt on the closure, the skirt extending from the closure in an upstream direction with respect to the flow of gas from the source.

6. Apparatus according to claim 1 or 2 which includes a plurality of closures adapted to be connected to a source of gas.

7. Apparatus according to claim 1 or 2 in which the source of gas under pressure is an electrically heated air blower.

8. Apparatus according to claim 7 which includes a chamber connected to the inlet through the closure, the chamber having an inlet, and a blower adapter mounted in the chamber inlet for making a snug fit around a discharge nozzle from the warm air blower.

9. Apparatus, according to claim 1 or 2 which includes a removable closure adapter constructed to make a slip fit over the exterior of the closure to increase the effective exterior diameter of the closure.

10. Apparatus according to claim 9 in which the closure adapter includes external grooves to provide an outlet for gas from the interior of the hand covering.

11. A method for drying a flexible, inflatable hand covering which is wet with a volatile liquid and which includes a finger section and an elastomeric wrist portion, the method including the steps of:
    stretching the wrist portion to make a snug fit around a closure;
    injecting a drying gas from an electrically heated blower through an inlet aperture in the closure and into the hand covering interior at a sufficient rate and temperature to inflate the finger section and vaporize liquid;
    removing the vapor-laden gas from the hand covering through at least one outlet port in the closure and spaced from the inlet aperture; and
    restricting the flow of gas from the outlet port to cause the hand covering to inflate.

12. A method according to claim 11 in which the gas is injected through a central portion of the closure.

13. A method according to claim 12 in which the gas is removed from the interior of the hand covering through a generally annular area surrounding the central portion of the closure.

* * * * *